United States Patent [19]
DeFreez et al.

[11] Patent Number: 6,111,642
[45] Date of Patent: Aug. 29, 2000

[54] FLOW APERTURED INTRACAVITY LASER PARTICLE DETECTOR

[75] Inventors: Richard K. DeFreez, Azalea; Kenneth L. Girvin; Frederic C. Schildmeyer, both of Grants Pass, all of Oreg.

[73] Assignee: Pacific Scientific Instruments Company, Grants Pass, Oreg.

[21] Appl. No.: 09/160,557

[22] Filed: Sep. 24, 1998

Related U.S. Application Data

[63] Continuation-in-part of application No. 09/113,986, Jul. 10, 1998, Pat. No. 6,016,194.

[51] Int. Cl.[7] ............................ G01N 21/00; G01N 15/06
[52] U.S. Cl. ............................................ 356/337; 250/574
[58] Field of Search ................................ 356/335, 336, 356/337, 338; 250/573, 574, 577

[56] References Cited

U.S. PATENT DOCUMENTS

| | | | |
|---|---|---|---|
| 4,746,215 | 5/1988 | Gross | 356/339 |
| 4,896,048 | 1/1990 | Borden | 250/574 |
| 5,085,325 | 2/1992 | Jones et al. | 209/580 |
| 5,565,984 | 10/1996 | Girvin | 356/336 |
| 5,642,193 | 6/1997 | Girvin et al. | 356/339 |
| 5,671,046 | 9/1997 | Knowlton | 356/338 |
| 5,726,753 | 3/1998 | Sandberg | 356/338 |
| 5,796,480 | 8/1998 | Igushi | 356/336 |

OTHER PUBLICATIONS

"Light Scattering Automatic Particle Counter", Japanese Industrial Standard, JIS B 9921, 1997.

*Primary Examiner*—Frank G. Font
*Assistant Examiner*—Michael P. Stafira
*Attorney, Agent, or Firm*—Stoel Rives LLP

[57] ABSTRACT

A particle counter (10) passes a sample stream of a carrier gas or fluid containing particles (72) through an elongated, flattened nozzle (16) and into a view volume (18) formed by an intersection of the sample stream and a laser beam (13). Particles entrained in the sample stream scatter light rays while passing through the view volume. The scattered light is collected by an optical system (26) and focused on to a detector (40). The magnitude of signal coming from the detector is indicative of the particle size. To correct for variances in particle velocity and light beam intensity across the view volume, flow aperturing is used. Flow aperture modeling (Eqs. 1–7) provides a format for designing the nozzle such that the lateral velocity profile matches the laser beam lateral intensity profile, thereby providing uniform detection sensitivity to laser light scattered from monodisperse particles distributed laterally across the view volume. Uniform detection sensitivity of monodisperse particles provides accurate particle sizing resolution.

12 Claims, 9 Drawing Sheets

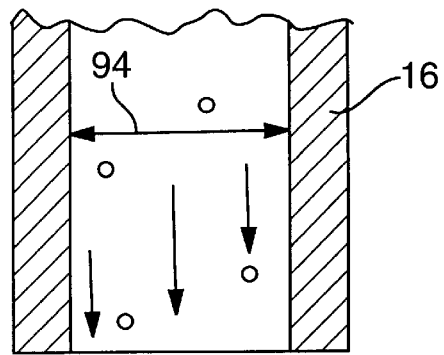
FIG. 3
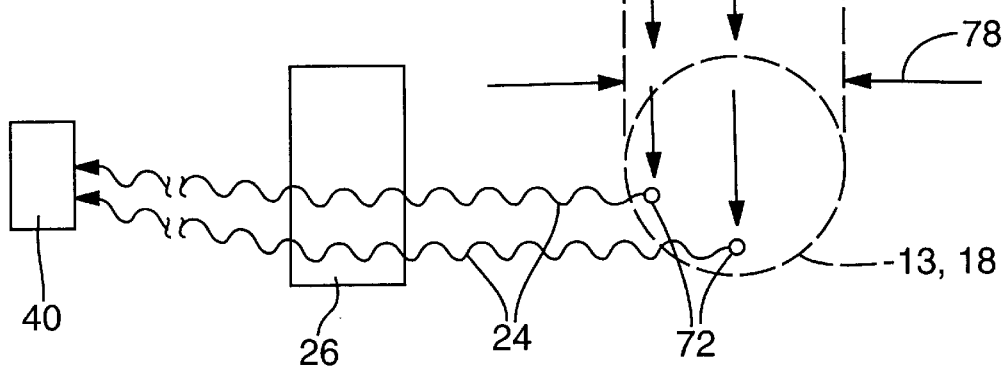
FIG. 6
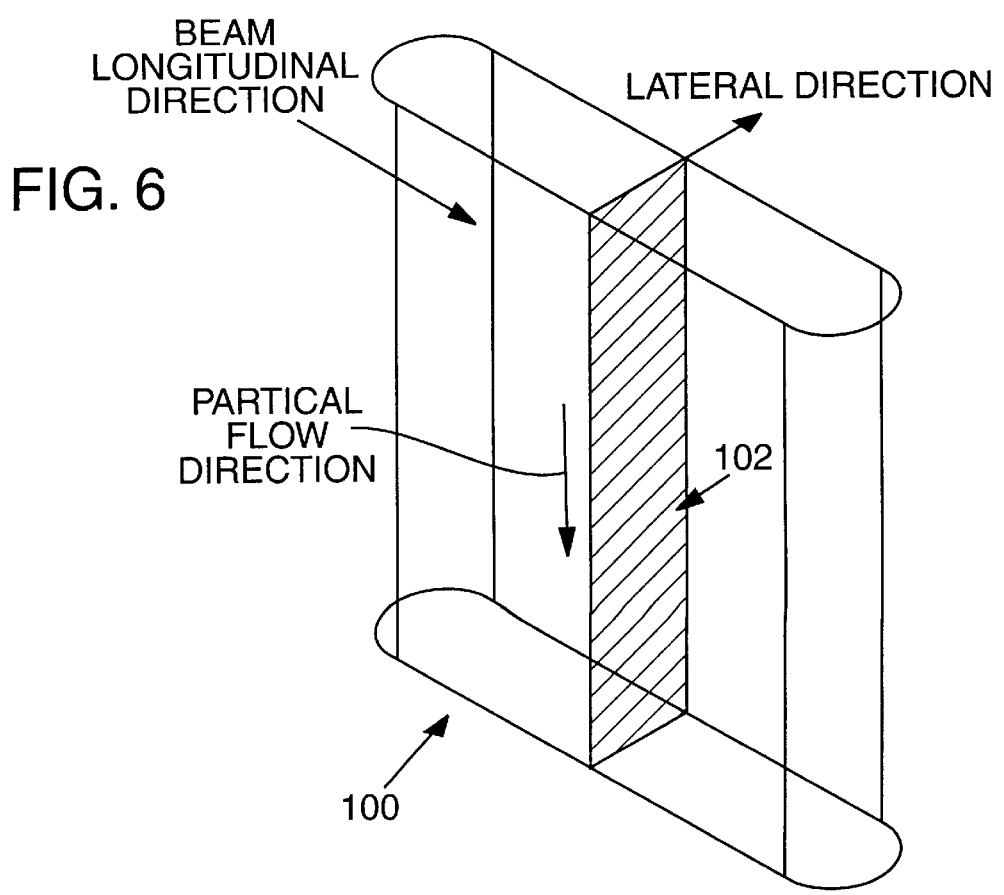

FLOW APERTURED INTRACAVITY LASER PARTICLE DETECTOR

RELATED APPLICATION

This application is a continuation-in-part of U.S. Pat. application Ser. No. 09/113,986, filed Jul. 10, 1998 now U.S. Pat. No. 6,016,194,for PARTICLE COUNTING APPARATUS AND METHOD HAVING IMPROVED PARTICLE SIZING RESOLUTION.

TECHNICAL FIELD

The present invention relates to optical particle detection and, in particular, to a flow aperture modeling technique for improving particle detection sensitivity and sizing resolution.

BACKGROUND OF THE INVENTION

Contamination control, including particulate monitoring, plays a critical role in the manufacturing processes of several industries. These industries require cleanrooms or clean zones with active air filtration and require a supply of clean raw materials such as process gases, deionized water, chemicals, and substrates. In the pharmaceutical industry, the Food and Drug Administration requires particulate monitoring because of the correlation between detected particles in an aseptic environment and viable particles that contaminate the product produced. Semiconductor fabrication companies require particulate monitoring as an active part of quality control. As integrated circuits become more compact, line widths decrease and wafer sizes increase such that the sizes of particulates causing quality problems become smaller. Accordingly, it is important to detect and accurately size submicron particles of ever-decreasing sizes and numbers per volumetric unit.

To perform particulate monitoring, currently commercially available submicron particle sensors use optical detection techniques to determine the presence, size, and/or number of particles in a volumetric unit. The basic building block for this technology is intracavity optical scattering of a laser beam and detection of the optical signal scattered by the particles. The standard particle detection approach, which was developed during the late 1980s, passes a sample stream containing the particles through an elongated flattened nozzle such that the sample stream exiting the nozzle intersects the laser beam in an area referred to as a view volume. Scattered light from particles in the view volume is collected with optics and focused onto the detection system.

U.S. Pat. No. 5,642,193 for PARTICLE COUNTER EMPLOYING A SOLID-STATE LASER WITH AN INTRACAVITY VIEW VOLUME, which is assigned to the assignee of this application, describes such a particle detection and counting system, and U.S. Pat. No. 4,746,215 for PARTICLE COUNTER AIR INLET ASSEMBLY describes a nozzle that produces a particle flow sample stream for developing a view volume in particle counting systems.

The nozzle, laser beam, and resulting view volume all have properties that affect particle detection sensitivity and sizing resolution. For example, the type of laser employed effects the laser beam lateral (transverse to the beam's longitudinal axis) intensity profile, with prior art multispatial mode HeNe lasers typically having a "top-hat" shaped lateral intensity profile. Such lasers have been used to provide sufficient intracavity optical power to produce readily detectable amounts of scattered light. To complement the laser beam top-hat intensity profile, the nozzles produce a turbulent flow having a substantially top-hat velocity profile where it intersects the laser beam, thereby producing an adequately uniform lateral particle detection sensitivity to support acceptable particle sizing resolution. Unfortunately, the turbulent nozzle flow produces intracavity noise in the view volume that degrades the particle detection signal-to-noise ratio. Reducing the nozzle flow rate to produce laminar flow results in a parabolic velocity profile that reduces intracavity noise but also degrades particle sizing resolution and overall particle detection rate.

What is needed, therefore, is a particle detection system having uniformly high particle detection sensitivity and sizing resolution throughout a view volume and, in particular, one that meets or exceeds the requirements set forth in "Light Scattering Automatic Particle Counter," JAPANESE INDUSTRIAL STANDARD JIS B 9921-1997 (the "JIS standard").

SUMMARY OP THE INVENTION

An object of the invention is, therefore, to provide a particle detection method and system that is characterized by high submicron particle detection sensitivity and accurate particle size determination.

Another object of this invention is to provide a particle detection system that provides uniform detection sensitivity to laser light scattered from monodisperse particles (evenly dispersed particles of the same size) distributed laterally across a view volume.

A further object of this invention is to provide a flow aperture modeling method for matching nozzle lateral flow profiles to laser lateral intensity profiles to provide uniform detection sensitivity to laser light scattered from monodisperse particles distributed laterally across a view volume.

A particle counter of this invention passes a sample stream of a carrier gas or fluid containing the particles through an elongated, flattened nozzle and into a view volume formed by an intersection of the sample stream and a laser beam. The nozzle has a lateral width dimension approximately equal to the laser beam lateral dimension at the view volume and a longitudinal dimension ranging from about the lateral dimension to greater than about 20 times the lateral dimension. Scattered light from the view volume is collected with optics and focused onto the detection system. A linear array of photodetector elements is employed in the detection system and positioned such that the longitudinal dimension of the view volume is imaged on the photodetector elements.

A flow aperture model of this invention is used to design the nozzle parameters so that its lateral flow profile matches the laser beam lateral intensity profile, thereby providing uniform detection sensitivity to laser light scattered from monodisperse particles distributed laterally across the view volume. Uniform detection sensitivity of monodisperse particles is essential to producing accurate particle sizing resolution.

Flow aperturing is generally defined as confining the particle-bearing sample stream to a lateral width approximately equal to or less than the lateral width of the intracavity laser beam, wherein the laser preferably operates in a lowest order Gaussian mode and the sample stream is preferably laminar. "Approximately equal to" means that the sample stream width is equal to or less than about 1.5 times the laser beam width. Flow aperture modeling of this invention allows a correlation between the sample stream lateral flow profile to the laser beam lateral intensity profile such that particles with higher velocities pass through higher intensity portions of the beam and slower particles pass through proportionally lower intensity portions of the beam. This causes a similar number of photons to be scattered by monodisperse particles independent of their lateral position in the view volume, thereby producing a uniform detector signal response for detecting monodisperse particles.

Single transverse mode lasers with spherical mirrors have a Gaussian lateral intensity profile. Laminar flow in the nozzle (Reynolds number less than about 2,000) produces a particle sample stream having a nearly parabolic lateral velocity profile where the sample stream exits the nozzle. However, within a relatively short distance the lateral velocity profile becomes nearly Gaussian, the precise distance being determined by the specific flow rate, the nozzle geometry, and the geometry of the area surrounding the view volume.

Typical light detection systems integrate the number of particle-scattered photons they receive from the view volume. When designed with flow aperture modeling, the laser beam lateral Gaussian intensity profile and sample stream lateral Gaussian velocity profile overlap, or match, and the resulting integrated scattered light is substantially constant versus the lateral position of the particles in the view volume.

Additional objects and advantages of this invention will be apparent from the following detailed description of preferred embodiments thereof that proceeds with reference to the accompanying drawings.

BRIEF DESCRIPTION OF THE DRAWINGS

FIG. 3 is an enlarged cross-sectional pictorial representation of the radiation beam, nozzle, collection optics, and photodetector of FIGS. 1 and 2 depicting the sensing of particles distributed laterally across the view volume of this invention.

FIG. 6 is an enlarged isometric pictorial representation of an exemplary nozzle having a 5:1 aspect ratio.

DETAILED DESCRIPTION OF PREFERRED EMBODIMENTS

Figure 1:
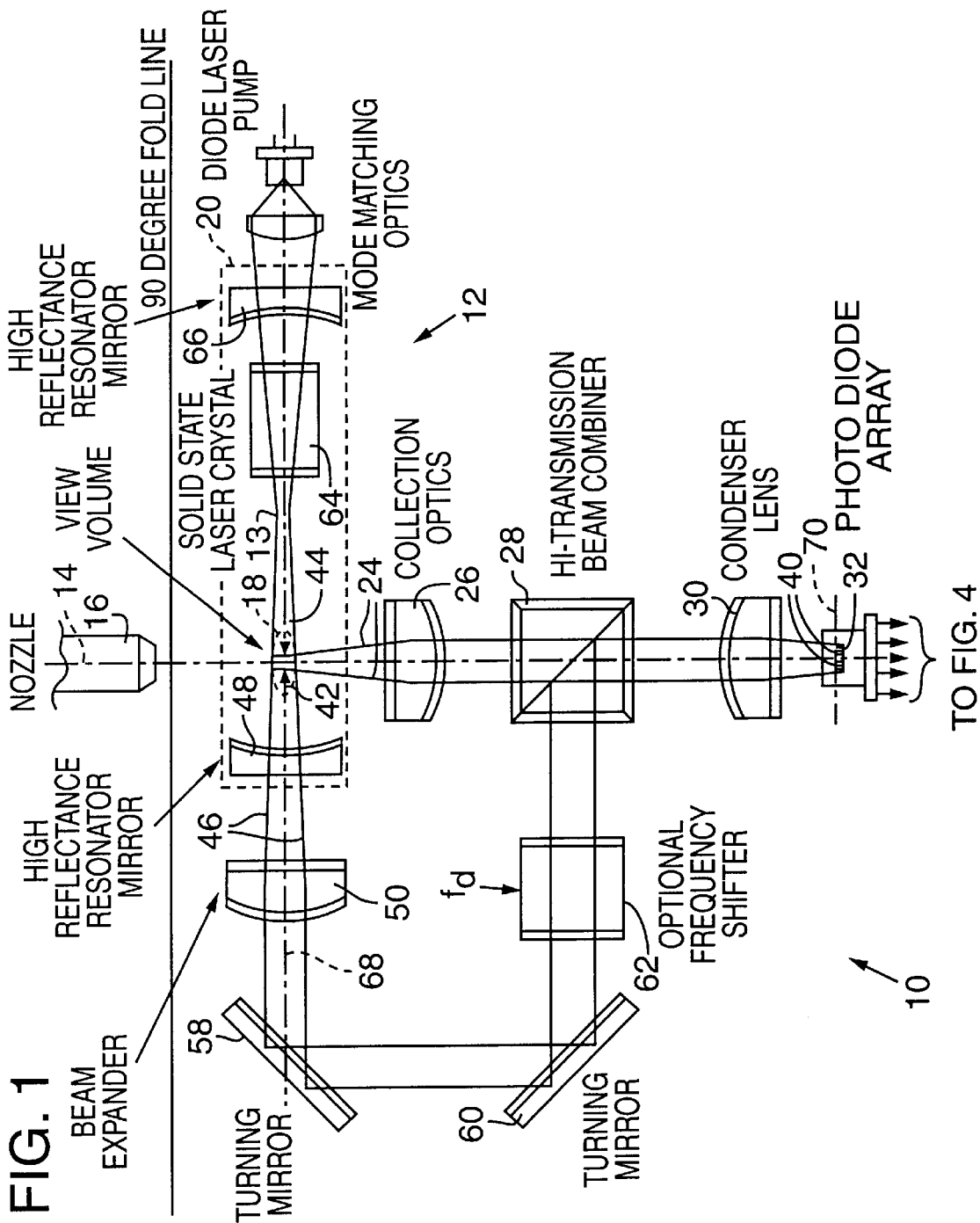
FIG. 1 is a block diagram of a high sensitivity airborne particle counter suitable for use with this invention.

FIG. 1 shows an airborne particle counter 10, which is suitable for use with this invention. This invention is also suitable for use with conventional airborne particle detection techniques, which are a subset of particle counter 10, and with liquid-borne particle detection techniques. Particle counter 10 includes a diode laser-pumped high intracavity intensity solid-state laser 12, which is robust, efficient, and compact and operates in the absence of high voltages and can be constructed to have high beam intensity and spectral qualities. (The invention can also be practiced with gas or dye lasers.) Laser 12 generates a laser beam 13 having an intracavity optical intensity that scatters radiation from particles injected in a flow direction 14 by an elongated, flattened nozzle 16 within a view volume 18 in a resonator 20 of laser 12. Particle-scattered light rays 24 are collected and collimated by collection optics 26, transmitted through a beam combiner 28, and then imaged by a condenser lens 30 onto a linear array 32 of photodiode detectors 40. Each of photodiode detectors 40 of linear array 32 detects the scattered light rays 24 from a longitudinal portion 42 surrounding a longitudinal axis 44 of laser beam 13 in view volume 18. Nonscattered light rays 46 simultaneously leak out of a left-hand side resonator mirror 48 and is collected, expanded, and collimated by a beam expander 50. An expanded beam of nonscattered light rays 46 is then redirected by a pair of turning mirrors 58 and 60 to beam combiner 28 from which it collinearly copropagates to condenser lens 30 where it is focused onto linear array 32 of photodiode detectors 40.

The detection technique implemented by particle counter 10 may be direct optical detection or a self-heterodyne or "homodyne" detection technique that uses the same optical oscillator to generate the signal (particle-scattered light rays 24) and the local oscillator (nonscattered light rays 46). Heterodyne detection entails developing a beat frequency signal between the particle-scattered light signal and the local oscillator in a square-law detector, such as photodiode detector 40. The beat frequency is selectively detected to the exclusion of other beat frequencies. The beat frequency for self-heterodyne detection is at zero frequency, i.e., a DC signal, which is known to be a particularly undesirable detection frequency because of 1/f noise. Shifting the beat frequency to some nonzero value in accordance with what is called an offset heterodyne technique eliminates the 1/f noise problem. Offset heterodyne detection can be accomplished by direct frequency shifting by means of an optional frequency shifter 62. A suitable frequency shifter 62 is an acousto-optic modulator receiving a drive signal $f_d$ that provides the offset frequency. The intracavity mode employed for heterodyne detection is preferably a high intracavity intensity, lowest order Gaussian mode derived from a half-symmetric spherical mirror resonator (not shown).

Laser resonator 20 contains a Cr:LiSAF crystal 64 and the curved resonator mirrors 48 and 66 with HR coatings (R~0.999965) to provide high intensity in a fundamental Gaussian mode. This configuration minimizes the number of optical elements and optical surfaces in resonator 20 and thus minimizes round-trip scattering and absorption losses. Single longitudinal mode control for a Cr:LiSAF lasing medium may require use of a spectral narrowing element in resonator 20 or use of injection locking to compensate for an insufficient etalon effect of Cr:LiSAF crystal 64.

To achieve improved sizing resolution, nozzle 16 sample stream flow rate can be reduced to produce a laminar flow.

Laminar flow in nozzle 16 (Reynolds number less than about 2,000) produces a particle sample stream having a nearly parabolic lateral velocity profile where the sample stream exits the nozzle. However, within a short distance, the lateral velocity profile becomes nearly Gaussian, the precise distance being determined by the specific flow rate, the nozzle geometry, and the geometry of the area surrounding the view volume. Consequently, in this invention, nozzle 16 may produce a Gaussian lateral velocity profile that complements the Gaussian intensity profile of laser beam 13.

Figure 2:
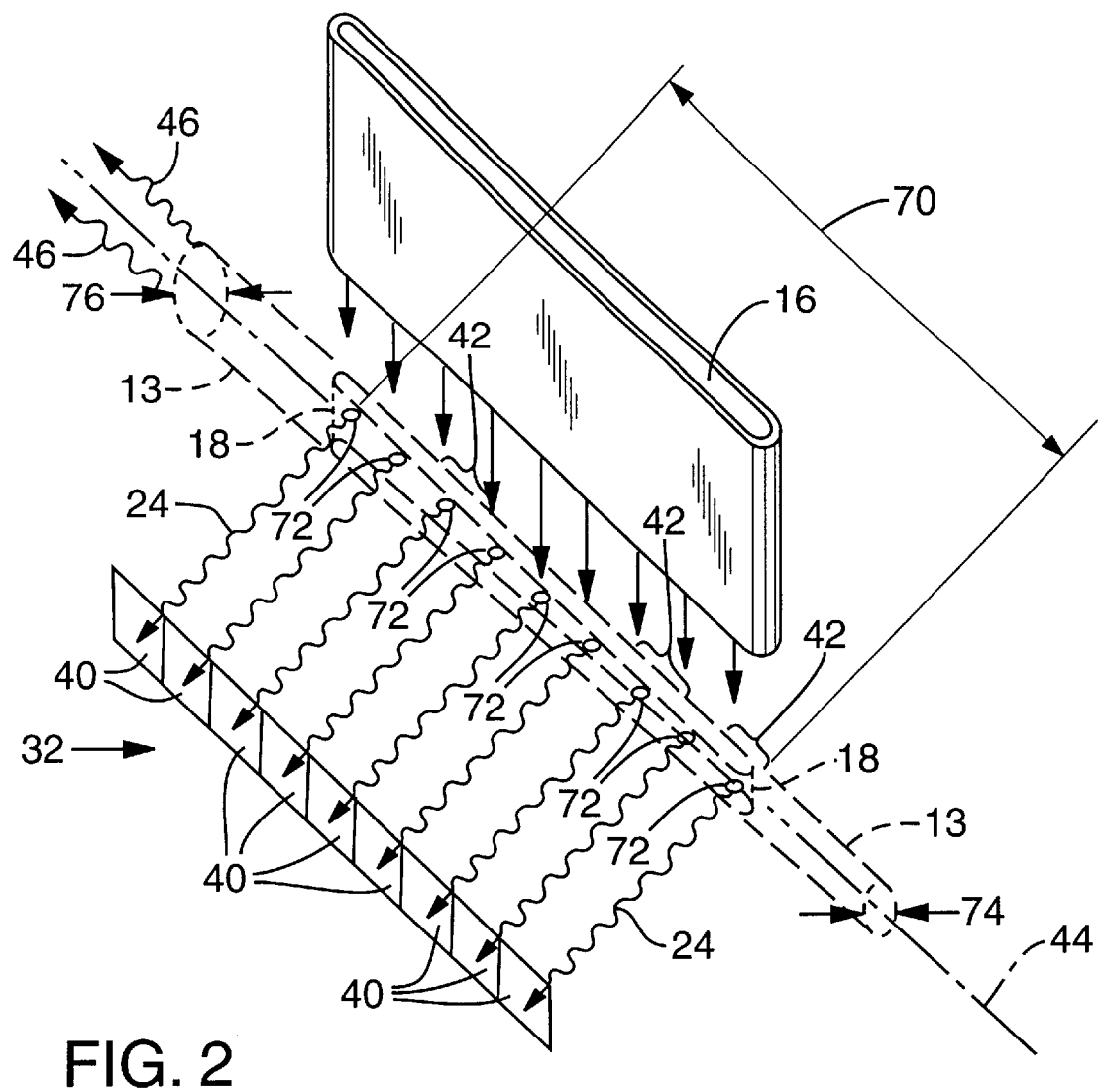
FIG. 2 is an enlarged isometric pictorial representation of a radiation beam, a nozzle, and a photodetector array arranged to sense particles distributed throughout a view volume of this invention.

Referring also to FIG. 2, particle counter 10 is preferably designed for detection efficiency and a high sample stream flow rate of about one cubic foot per minute. The efficiency of the detection system is inversely proportional to its angular field of view. This is true because the optical heterodyne efficiency is inversely proportional to the integral of the phase difference between the local oscillator field and scattered signal wavefronts over the surface of a photodiode detector 40. In short, large detectors lead to larger integrals or lower intensity heterodyne signals. On the other hand, the sample stream flow rate of intracavity particle counter 10 is proportional to a longitudinal length 70 of view volume 18. Because particle counter 10 employs a linear array 32 of photodiode detectors 40, many parallel detection channels are created, which allow for a relatively long longitudinal length 70 of view volume 18 while maintaining the efficiency of the detection system.

The detection system uses linear array 32 of photodiode detectors 40 having dimensions that are proportional to the image dimensions of view volume 18. Linear array 32 is arranged such that scattered light from each of the particles 72 passing through view volume 18 is imaged (optics not shown in FIG. 2) onto one of photodiode detectors 40 corresponding to that area of view volume 18. The height of each detector 40 is proportional to the distance the particle travels laterally through view volume 18 and the length of linear array 32 is proportional to longitudinal length 70 of view volume 18. The width of each detector 40, and the gap between them, is minimized to provide increased phase overlap between particle-scattered light rays 24 and nonscattered light rays 46.

The detection system works well for the majority of particles 72 ejected from nozzle 16, which is implemented along the lines described in U.S. Pat. No. 5,746,215 for PARTICLE COUNTER AIR INLET ASSEMBLY.

Particle sizing resolution depends on each of photodiode detectors 40 generating pulses that accurately represent the sizes of particles 72. However, detectors 40 integrate received photons to generate ramped pulses having magnitudes (amplitude times pulse duration) that are proportional to the time it takes particles 72 to traverse view volume 18, the sizes of particles 72, the intensity of laser beam 13, and the sensitivity of each detector 40. Unfortunately, nozzle 16 produces a sample stream velocity profile that causes particles 72 to have different velocities (shown as various length vectors exiting nozzle 16) depending on their longitudinal passage position through view volume 18. Also, the intensity of laser beam 13 is not longitudinally constant along view volume 18 because of beam divergence (shown as a difference in laser beam 13 waist diameters 74 and 76). Moreover, the sensitivities of detectors 40 are typically nonuniform across linear array 32 and the light collection optics nonuniformly reproduce on detector 40 image intensities generated in view volume 18. Solutions to these problems are addressed in copending U.S. Pat. application Ser. No. 09/113,986 for PARTICLE COUNTING APPARATUS AND METHOD HAVING IMPROVED PARTICLE SIZING RESOLUTION, which is assigned to the assignee of this application.

Referring to FIG. 3, nozzle 16 likewise produces a sample stream velocity profile that causes particles 72 to have different velocities (shown as various length vectors exiting nozzle 16) depending on their lateral passage position through view volume 18. Also, the intensity profile of laser beam 13 (shown here coincident with laser beam 13) is not constant laterally across a width 78 of view volume 18 because of the operational mode of laser 12. The intensity profile may be Gaussian or have some other profile depending on the operational mode chosen.

Because nozzle 16 produces nonuniform particle velocities across width 78 of view volume 18, for equally sized particles 72, higher velocity particles have a lesser time in view volume 18 and, therefore, cause detectors 40 to generate lower magnitude output signals than slower velocity particles. The problem is made worse by the nonuniform lateral intensity profile of laser beam 13. In this invention, however, flow aperture modeling, which is described with reference to Eqs. 1–8 and FIGS. 5–11, enables overlapping, or matching, the nozzle 16 flow velocity profile and the laser beam 13 intensity profile to cause a uniform particle 72 detection sensitivity laterally across width 78 of view volume 18.

Figure 4:
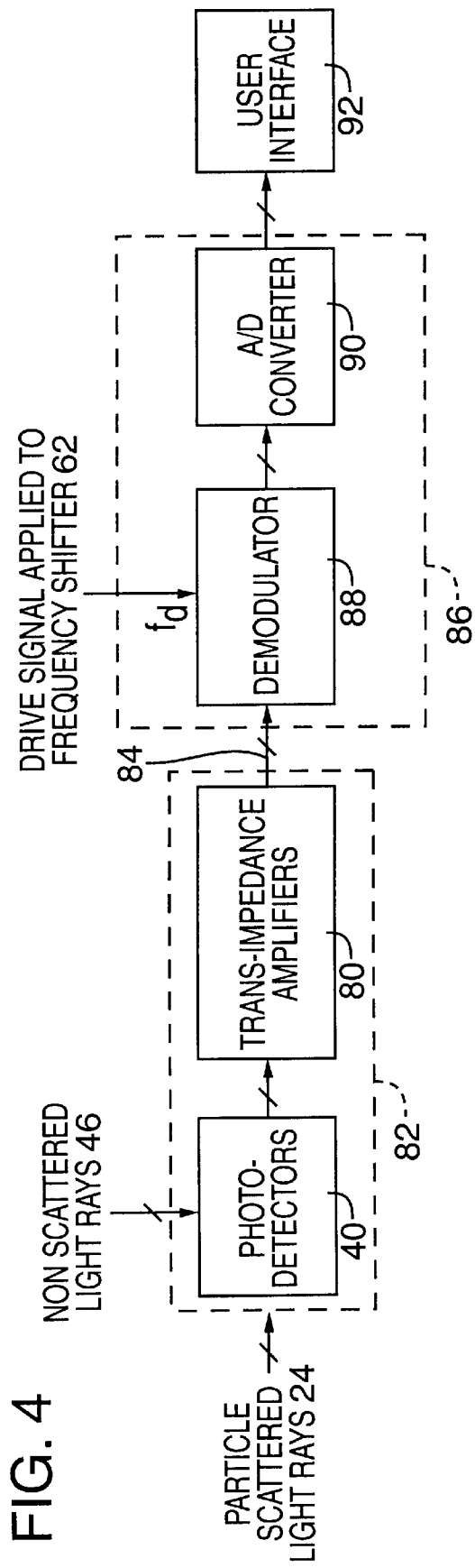
FIG. 4 is a block diagram showing the processing of signals derived from particle-scattered light rays in accordance with this invention.
Figure 5:
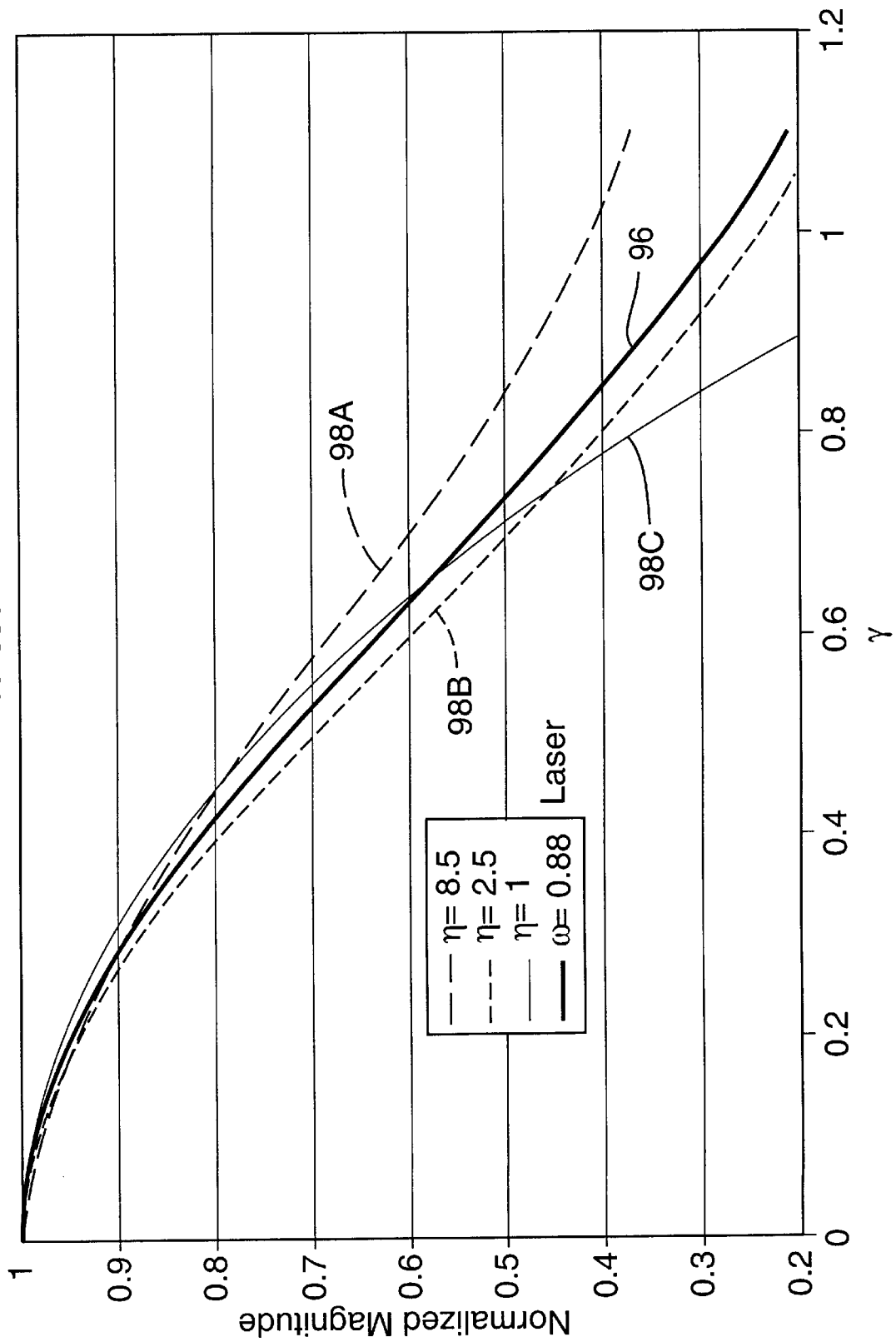
FIG. 5 graphically depicts a family of nozzle flow velocity profiles compared to a laser beam intensity profile.
Figure 7:
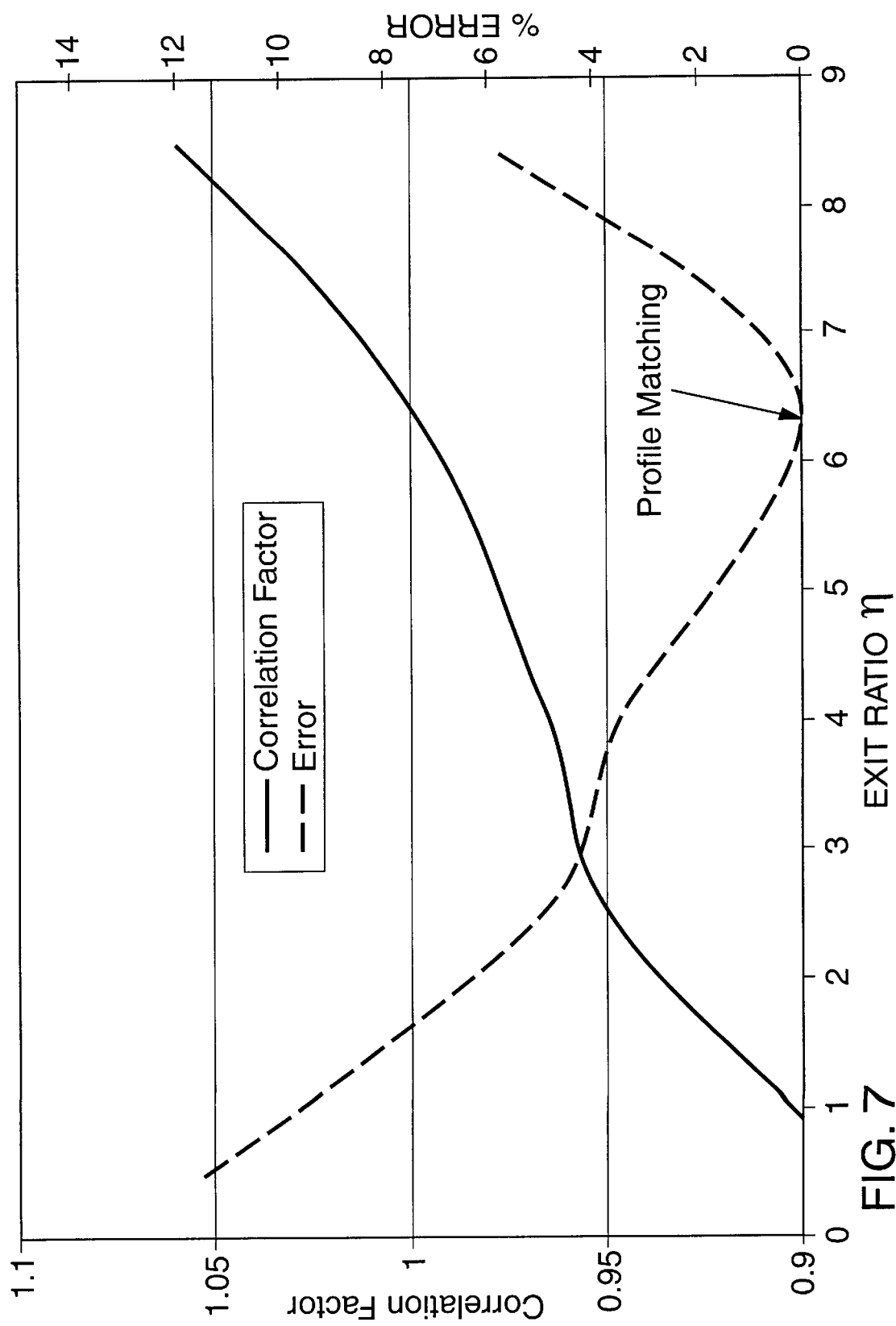
FIG. 7 graphically depicts how a flow aperture correlation of this invention varies as a function of a nozzle exit ratio of this invention.

Before describing flow aperture modeling, FIG. 4 shows in block diagram form the detection and processing of signals derived from particle-scattered light rays 24 and nonscattered light rays 46. Each detector 40 is connected to a transimpedance amplifier 80 to form a photo-amplifier 82. When detecting particles 72, each detector 40 receives two optical carriers, one from particle-scattered light rays 24 and one from nonscattered light rays 46. The combined light, if the offset heterodyne technique is employed, has a DC magnitude and a dominant beat frequency. The particle-scattered light carrier then becomes directly amplitude modulated as a particle traverses the laser beam. The resulting amplitude modulation of the dominant beat frequency contains particle sizing information. Each photo-amplifier 82 generates an output signal 84 that is post-processed by processing circuitry 86, which includes demodulation electronics 88 and an analog-to- digital converter 90, to extract the signal amplitude representing the particle-scattered light. The drive signal $f_d$ applied to frequency shifter 62 to provide the offset frequency is used by demodulation electronics 88 to tune in the resulting optical carrier beat frequency. Analog-to-digital converter 90 converts the extracted analog signals to digital signals. The signal amplitude of the extracted signal represents the size of the particle. Repetitive signals represent the number of particles.

The resulting signals are directed to a user interface 92, as is typically done in conventional particle counters. The digital signals represent the size and number of the particles that pass through view volume 18.

In direct optical particle detection systems, the relationship of particle size to optical size is proportional to $d^6$, where d is the particle diameter. The particle size-to-signal relationship in heterodyne detection is proportional to $d^3$. Therefore, heterodyne detection has the advantage of increasing by a power of two the dynamic range of particle size detection. However, flow aperture modeling is applicable to either detection system.

Regarding flow aperture modeling, the sample stream velocity and laser beam intensity profiles are repeatable, predictable and measurable and may, therefore, be determined and controlled. Referring again to FIGS. 1–4, for flow aperture modeling to apply to a particle counter, for example particle counter 10 (FIG. 1), nozzle 16 (FIG. 3) has a lateral width 94 that is selected to provide a velocity profile across view volume 18 that correlates to a constant scattering function independent of the lateral location of particles 72 in laser beam 13. Fast moving particles passing through the central more intense, region of laser beam 13 have a shorter flight time than slower moving particles passing through the outer, less intense, region of laser beam 13. A flow apertured system is achieved when the amount of scattered light rays 24 scattered by spatially distributed monodisperse particles is nearly constant. When this occurs, the integrated magnitude of photo-amplifier output signals 84 (FIG. 4) resulting from the monodisperse particles passing though view volume 18 is substantially a constant.

A preferred Gaussian flow aperture modeling example employs a nozzle 16 with a laminar sample stream flow and laser 12 operating in single transverse $TM_{00}$ mode. The laminar sample stream flow discharges from nozzle 16 into a static ambient environment composed of the same fluid, for example, air. The velocity profile of the discharged fluid transforms from a parabolic profile inside nozzle 16 to a nearly Gaussian velocity profile outside nozzle 16. The velocity profile transformation is non-discrete and is typically fully developed at distances from nozzle 16 greater than about four times nozzle lateral width 94.

Designing an approximate flow aperture match between nozzle 16 and laser beam 13 entails predicting sample stream width 78 at view volume 18 for a given nozzle 16 lateral width 94 and a mean sample stream velocity. The predicted sample stream width 78 is then used to match the waist diameter of the laser beam 13 $TEM_{00}$ intensity profile at view volume 18.

Eqs. 1, 2, and 3 represent three ratios that characterize the sample stream flow conditions from nozzle 16.

$$\text{Exit Ratio} = \eta = \frac{z}{d} \qquad \text{Eq. 1}$$

where z is the distance from the end of nozzle 16 to view volume 18, and d is its lateral width 94.

$$\text{Lateral Ratio} = \gamma = \frac{2*x}{d} \qquad \text{Eq. 2}$$

where x is the lateral distance from nozzle center at any given distance from the nozzle end.

$$\text{Reynolds Number} = R = \frac{v*d*\rho}{\mu} \qquad \text{Eq. 3}$$

where v is the mean velocity of sample stream from nozzle 16, p is the sample stream fluid mass density, and $\mu$ is the sample stream fluid viscosity.

FIG. 5 shows a laser mode intensity profile 96 contrasted to a family of sample stream velocity profiles 98A, 98B, and 98C each representing a different exit ratio η.

Eq. 4 represents a velocity waist equation expressed as a function of the exit ratio and the Reynolds number. Eq. 4 is derived from analytical and/or experimental data.

$$\text{Velocity Waist Function} = W_{velocity} = f(\eta, R) \qquad \text{Eq. 4}$$

A nozzle having an aspect ratio greater than one is oriented parallel and adjacent to longitudinal axis 44 of laser beam 13. For example, FIG. 6 shows a nozzle 100 having a 5:1 aspect ratio. A two dimensional slice 102 is employed to approximate the velocity waist function, and a three dimensional summation of two-dimensional slices is employed to accurately predict the waist function's longitudinal dependence. The flow aperture in two dimensional slice 102 is determined from a correlation factor C represented by Eq. 5. When correlation factor C equals 1, the nozzle velocity profile and the laser intensity profile are matched.

$$\text{Correlation Factor} = C = \frac{W_{velocity}}{W_{laser}} \qquad \text{Eq. 5}$$

FIG. 7 shows correlation factor C of Eq. 5 plotted for an exemplary two-dimensional slice 102 (FIG. 5) in which the laser beam waist is 880 microns and the nozzle 100 Reynolds number is 650. The minimum percent error between the laser waist and the sample stream waist readily identifies the optimal laser beam location.

In the three dimensional case, correlation is approximated by a weighted series summation represented in Eq. 6. The coefficient $a_j$ for each correlation cross-section is numerically or experimentally determined.

$$\text{Series Correlation} = C_s = \Sigma a_j * C_j \qquad \text{Eq. 6}$$

Eq. 7 represents, in a third order power series, an estimated exit ratio dependence of the velocity waist for a sample stream flow from a nozzle in which the Reynolds number is 650.

$$W_{velocity}^{650} = d*(0.759+0.0472*\eta-0.0085*\eta^2+0.00063*\eta^3) \qquad \text{Eq. 7}$$

Eq. 7 predicts the lateral velocity waist at any point along the transverse direction of a nozzle. Selecting an exit ratio defines the flow aperture for which the laser beam correlates.

The waist diameter of laser beam 13 where it intersects view volume 18 is represented by Eq. 8, which is derived from the following four relationships for laser resonators that are described in APPLIED OPTICS, Kogehnik and Li, October 1966. In the following equations:

laser resonator length units are in centimeters, laser beam units are in microns,

R1 is the first resonator mirror radius,

R2 is the second resonator mirror radius, d is the distance between the first and second mirrors, λ is the laser wavelength, n is the index of refraction of the space between the mirrors, ω1 is the radius of the laser beam to $1/e^2$ at the first mirror, ω2 is the radius of the laser beam to $1/e^2$ at the second mirror, ω0 is the radius of the laser beam to $1/e^2$ at its waist, ωV is the radius of the laser beam to $1/e^2$ at the view volume, and z is the distance from the waist to the view volume.

In the example calculated below, R1 is 24.13, R2 is 1,000,000, d is 23.9, λ is $0.83*(10)^{-4}$, z is $2.1*(10)^5$, and n is 1.

$$\omega 1 = \left[\left(\frac{\lambda * R1}{\pi}\right)^2 * \left(\frac{R2-d}{R1-d}\right) * \left(\frac{d}{R1+R2-d}\right)\right]^{0.25} * (10)^4$$

-continued $\omega 1 = 806$ microns $$\omega 2 = \left[\left(\frac{\lambda * R2}{\pi}\right)^2 * \left(\frac{R1-d}{R2-d}\right) * \left(\frac{d}{R1+R2-d}\right)\right]^{0.25} * (10)^4$$

$\omega 2 = 79$ microns $$\omega 0 = \left[\left(\frac{\lambda}{\pi}\right)^2 * \left(\frac{d(R1-d)(R2-d)(R1+R2-d)}{(R1+R2-2d)^2}\right)\right]^{0.25} * (10)^4$$

$\omega 0 = 79$ microns $$z0 = \frac{\pi * \omega 0^2 * n}{\pi(10)^4}$$

$z0 = 2.34(10)^4$ microns

The beam waist diameter 6)z at any location z measured in microns from ω0 is represented by Eq. 8. In this example, z equals $2.1*(10)^5$ microns and, therefore, the beam waist diameter at the view volume is:

$$\omega V = \omega 0 \left[1 + \left(\frac{z}{z0}\right)^2\right]^{.5} \quad \text{Eq. 8}$$

$\omega V = 709$ microns.

COMPARATIVE EXAMPLES

Set forth below are two comparative examples of simulated particle detector performance with and without flow aperture modeling applied. In the example without flow aperture modeling applied, the sample stream flow radius is 2.5 times the laser beam radius, whereas in the example implemented with flow aperture modeling, the sample stream flow radius is 1.1 times the laser beam radius. The examples are intended to show that particle detector performance should be improved when the $1/e^2$ distances of the laser beam intensity profile and the sample stream velocity profile approximately match at the view volume.

In actual implementations, the radius of the laser beam would be calculated using Eq. 8, and the corresponding lateral width of the nozzle would then be calculated using Eq. 7. In the following comparative examples, the laser beam radius is set at a normalized 1 unit value. The comparative simulations were set up employing the parameters set forth in Table 1.

TABLE 1

|  | Without FA Model | With FA Model |
|---|---|---|
| n = Number of pulses | 20,000 | 20,000 |
| ω0 = Laser beam radius | 1 | 1 |
| mf = Sample stream-to-beam radius ratio | 2.5 | 1.1 |
| ωf = ω0*mf = Sample stream flow radius | 2.5 | 1.1 |
| fracg = Laser beam fractional spatial noise | 0.05 | 0.05 |
| fracf = Flow fractional spatial noise | 0.02 | 0.02 |
| pvar = Particle fractional half-size variation | 0.032 | 0.032 |
| ωvar = Beam mdius fractional longitudinal variation | 0.02 | 0.02 |
| i = 1 . . . n |  |  |

The following calculations were performed for values of i from 1 to 20,000 for each set of parameters.

Singlet particle signal for a stationary particle at the $i_{th}$ location:

$$inglg_i = e^{\frac{-2i^2}{(\omega 0_2^n)^2}} \left[\left(1 + rnd(fracg) - \frac{fracg}{2}\right)\right.$$
$$\left. (1 + rnd(2pvar) - pvar)^6 (1 + rnd(2\omega var) - \omega var)^2\right]$$

Reciprocal velocity for the $i_{th}$ location particle:

$$velinv_i = e^{\frac{2i^2}{(\omega f \frac{n}{2})^2}} \left(1 + rnd(fracf) - \frac{fracf}{2}\right)^{-1}.$$

The integrated signal $Il_i$ for the $i_{th}$ location singlet particle equals the product of the above two equations: $Il_i = singlg_i * velinv_i$.

Figure 8A:
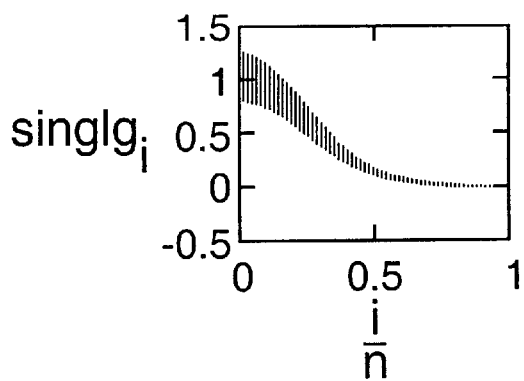
FIGS. 8A, 8B, and 8C graphically depict simulated signal detection sensitivity of a conventional particle detector example.
Figure 8B:
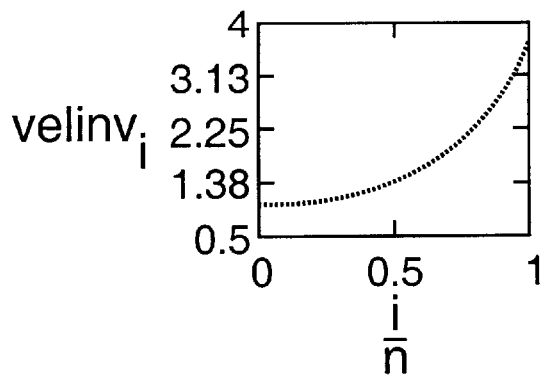
Figure 8C:
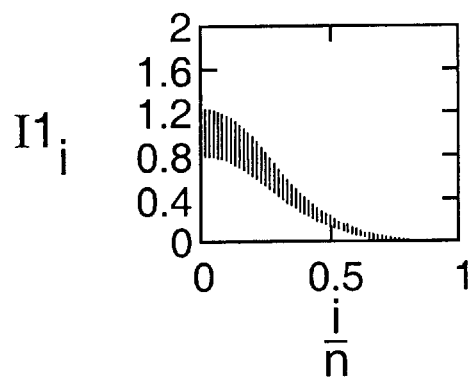
Figure 9A:
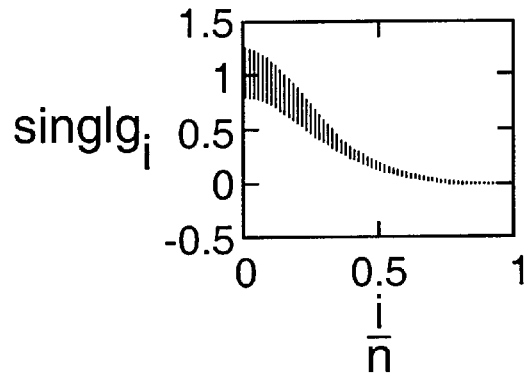
FIGS. 9A, 9B, and 9C graphically depict corresponding simulated particle detection sensitivity of a particle detector example employing flow aperture modeling of this invention.
Figure 9B:
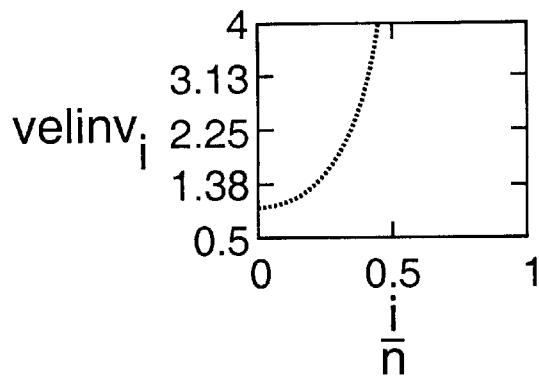
Figure 9C:
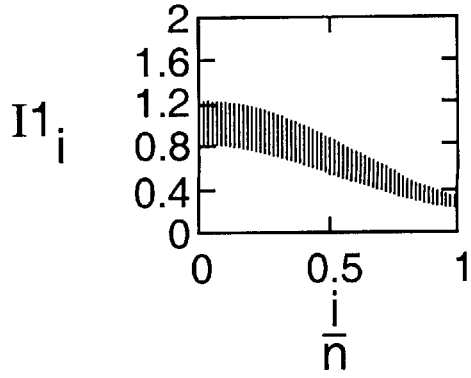

The results of the above simulation calculations for the example without flow aperture modeling are represented by the graphs in FIGS. 8A, 8B, and 8C, and the respective comparative results for the example with flow aperture modeling are represented by the graphs in FIGS. 9A, 9B, and 9C. The signal graphs of FIGS. 8A and 9A when multiplied by the respective integration time graphs of FIGS. 8B and 9B result in the respective integrated signal graphs of FIGS. 8C and 9C.

Next, comparative multichannel analyzer histogram simulations were set up and run employing the following parameters for both examples: N=600, j=1 . . . N, k-1 . . . N-1, m=4.0, channel1$_j$=(m*j)/N, and counts1=hist (channel1, I1), where "channel" represents voltages that correspond to particle pulse amplitudes created from the particle signals that pass through the analog circuitry, and "counts" represents the number particle pulses in the channel.

The probability density for a particle at the $k_{th}$ location is represented by:

$$density1_k = e^{\frac{-2\left(\frac{m*n*k}{N}-n\right)^2}{(\omega f \frac{n}{2})^2}}.$$

Figure 10A:
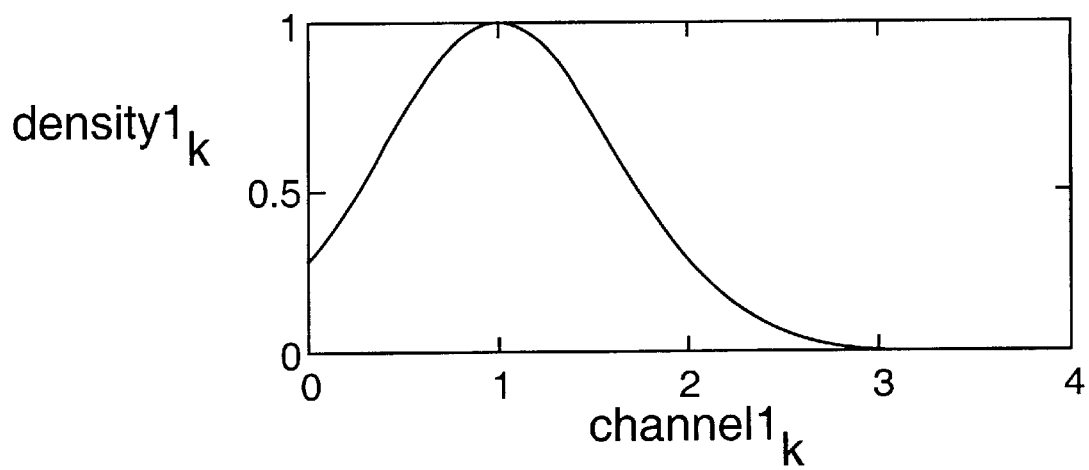
FIGS. 10A, 10B, and 10C graphically depict a simulated multichannel analysis of particle counting performance for the conventional particle detector example.
Figure 11A:
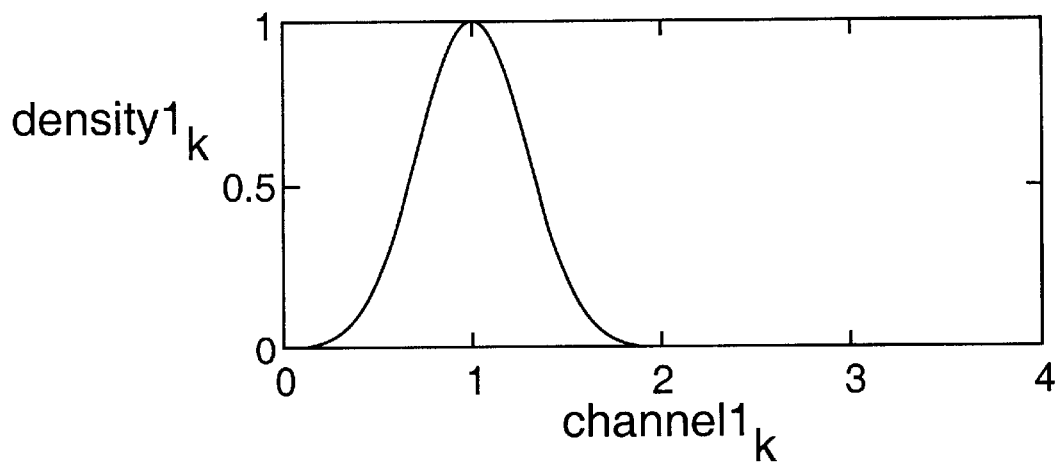
FIGS. 11A, 11B, and 11C graphically depict a corresponding simulated multichannel analysis of particle counting performance for the particle detector example employing flow aperture modeling of this invention.

FIGS. 10A and 11A show the resulting graphs of particle probability density for the respective examples without and with flow aperture modeling. As expected, because of its higher sample stream flow-to-laser beam radius ratio, the particle probability density of FIG. 10A shows a broader Gaussian particle distribution than the distribution of FIG. 11A.

Figure 10B:
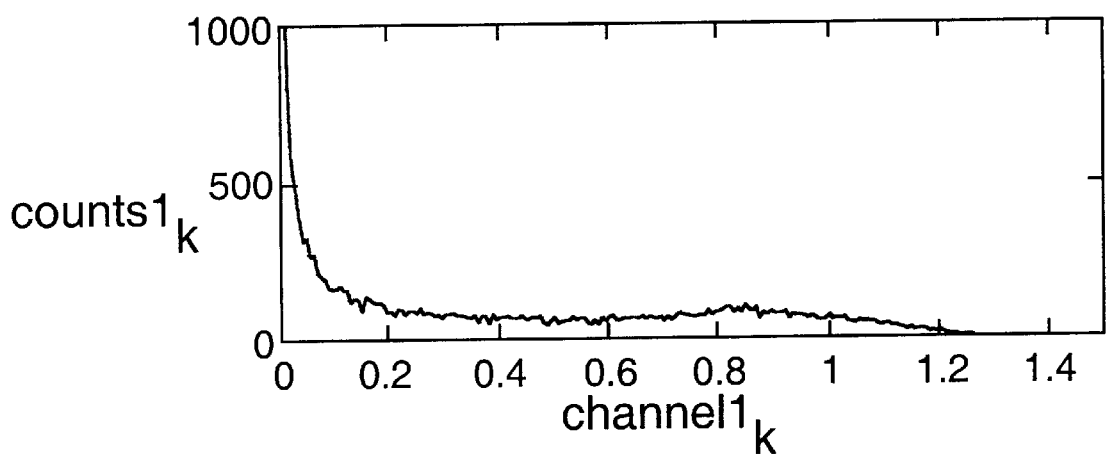
Figure 11B:
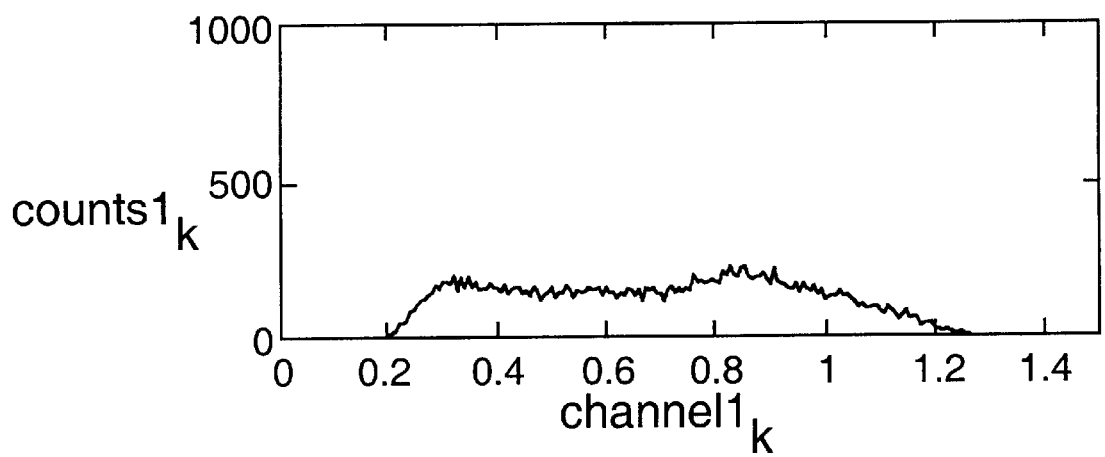

FIGS. 10B and 11B show the resulting graphs of counts prior to consideration of the lateral particle number density distribution.

Figure 10C:
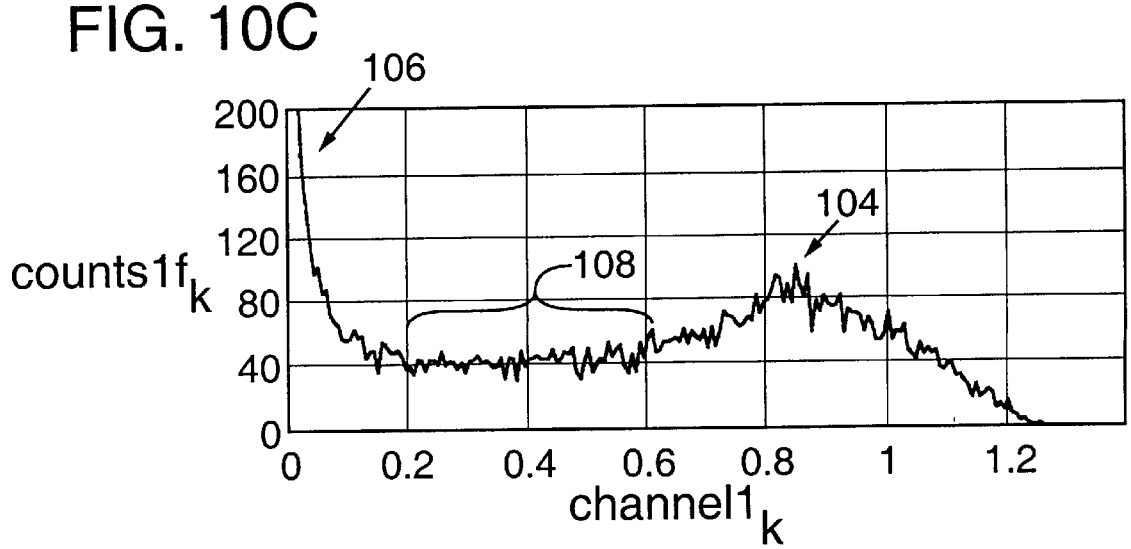
Figure 11C:
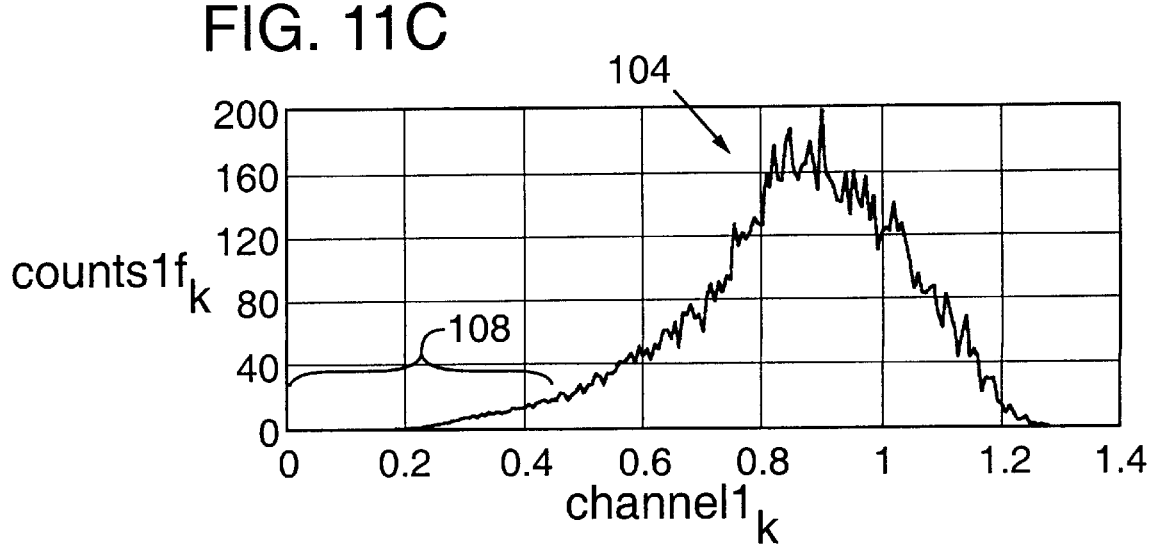

FIGS. 10C and 11C show the counts in $k_{th}$ channel graphs that result from multiplying the graph values of FIGS. 10A and 11A by the respective graph values of FIGS. 10B and 11B. (To aid in visual interpretation, note that FIGS. 10A and 11A have an wider horizontal scale factor than FIGS. 10B, 10C, 11B, and 11C.) Expressed mathematically, the graphs of FIGS. 10C and 11C result from calculating the equation: counts1f$_k$=density1$_k$*counts1$_k$.

Comparing FIGS. 10C and 11C, a peak 104 indicative of the particle output amplitudes stands out away from the "0" channel when the flow-to-laser radius ratio is reduced from 2.5 (FIG. 10C) to 1.1 (FIG. 11C). In FIG. 10C a significant peak 106 exists in the "0" channel, which is caused by many particles passing through the edge of the beam creating low amplitude pulses.

Also, a particle detector signal-to-noise ratio is dramatically improved as measured by a count ratio, which is described in the JIS standard as the ratio of the number of counts in peak channel 104 to the number of counts in a lowest channel in a range of channels 108 between the peak and the noise.

Another particle counter performance metric described in the JIS standard is counting efficiency. To calculate the counting efficiency of each example, assume a noise floor of 0.1 times the channel 1 width and find the fraction of counts above the noise floor by employing the following equation:

$$\text{Counting Efficiency} = \frac{\sum_{k=15}^{300} counts\, If_k}{\sum_{k=1}^{300} counts\, If_k}.$$

The counting efficiency of the example with flow aperture modeling exceeds 99 percent, which is significantly greater than the 84 percent counting efficiency of the example without flow aperture modeling. A counting efficiency greater than about 90 percent is readily achieved with this invention.

Flow aperture modeling of this invention is advantageous because it provides a technique for approximately matching the nozzle lateral velocity profile at the view volume to the laser beam lateral intensity profile.

Flow aperture modeling of this invention is further advantageous because it improves the particle counting and sizing accuracy of particle counters, such as particle counter 10, and helps them meet or exceed the particle counter requirements set forth in the JIS standard.

Skilled workers will recognize that portions of this invention may be implemented differently from the implementations described above for preferred embodiments. For example, sample stream turbulent flow from the nozzle can also be modeled and approximately matched to the laser beam intensity profile. Because turbulent flow approximates a narrow "top hat"-like profile at the view volume, approximate matching would require the sample stream flow width to be bounded within the laser beam Gaussian intensity profile. Skilled workers could also apply flow aperture modeling to other applications where the beam diameter, beam shape, sample stream flow rate, and nozzle lateral velocity profile differ from those described above.

It will be obvious to those having skill in the art that many changes may be made to the details of the above-described embodiments of this invention without departing from the underlying principles thereof. The scope of the present invention should, therefore, be determined only by the following claims.

We claim:

1. An optical particle detection system, comprising:
   a laser generating a beam of coherent radiation having a beam lateral dimension and a beam lateral intensity profile;
   a nozzle having a nozzle lateral dimension equal to or less than about 1.5 times the beam lateral dimension and providing a sample stream of target particles that pass transversely through the laser beam, the sample stream having a stream lateral velocity profile that substantially matches the beam lateral intensity profile;
   a view volume formed by the intersection of the laser beam and the sample stream, the target particles in the view volume scattering a quantity of the coherent radiation propagating through the view volume so that particle-scattered radiation exits the view volume; and
   a radiation-sensitive detector receiving the particle-scattered radiation and generating output signals indicative of a number and a size of the target particles passing through the view volume.

2. The system of claim 1 in which the nozzle lateral dimension ranges from about 0.9 to about 1.1 times the beam lateral dimension.

3. The system of claim 1 in which the beam lateral intensity profile and the nozzle lateral velocity profile have a substantially Gaussian shape.

4. The system of claim 1 in which the radiation-sensitive detector further receives a signal derived from the beam of coherent radiation and mixes the signal and the particle-scattered radiation to perform heterodyne detection of the target particles.

5. The system of claim 1 in which the target particles are monodisperse particles that pass through various lateral locations of the view volume and the output signals have substantially equal magnitudes.

6. The system of claim 1 further having a counting efficiency greater than about 90 percent.

7. An optical particle detection method, comprising:
   generating a beam of coherent radiation having a beam lateral dimension and a beam lateral intensity profile;
   providing a nozzle having a nozzle lateral dimension equal to or less than about 1.5 times the beam lateral dimension;
   ejecting from the nozzle a sample stream of target particles that pass transversely through the laser beam, the sample stream having a stream lateral velocity profile that substantially matches the beam lateral intensity profile;
   forming a view volume at the intersection of the laser beam and the sample stream, the target particles in the view volume scattering a quantity of the coherent radiation propagating through the view volume so that particle-scattered radiation exits the view volume; and
   detecting the particle-scattered radiation and generating output signals indicative of a number and a size of the target particles passing through the view volume.

8. The method of claim 7 in which the nozzle lateral dimension ranges from about 0.9 to about 1.1 times the beam lateral dimension.

9. The method of claim 7 in which the beam lateral intensity profile and the nozzle lateral velocity profile have a substantially Gaussian shape.

10. The method of claim 7 in which the detecting further includes receiving a signal derived from the beam of coherent radiation and mixing the signal and the particle-scattered radiation to perform heterodyne detection of the target particles.

11. The method of claim 7 in which the target particles are monodisperse particles that pass through various lateral locations of the view volume and the output signals have substantially equal magnitudes.

12. The method of claim 7 further having a counting efficiency greater than about 90 percent.

* * * * *